United States Patent [19]

Fogarty

[11] Patent Number: 4,643,194
[45] Date of Patent: Feb. 17, 1987

[54] FLEXIBLE CALIBRATOR

[75] Inventor: Thomas J. Fogarty, 770 Welch Rd., Palo Alto, Calif. 94304

[73] Assignee: Thomas J. Fogarty, Palo Alto, Calif.

[21] Appl. No.: 339,317

[22] Filed: Jan. 15, 1982

Related U.S. Application Data

[63] Continuation of Ser. No. 114,979, Jan. 24, 1980.

[51] Int. Cl.$^4$ .............................................. A61B 5/10
[52] U.S. Cl. .................................... 128/668; 128/774; 128/772; 33/512
[58] Field of Search ............... 128/772, 774, 778, 780, 128/DIG. 9, 668, 325; 604/95, 104, 164, 170; 33/174 D

[56] References Cited

U.S. PATENT DOCUMENTS

| | | | |
|---|---|---|---|
| 2,393,003 | 1/1946 | Smith | 604/170 |
| 3,128,769 | 4/1964 | Scislowicz | 604/170 |
| 3,528,404 | 9/1970 | Jeckel | 128/772 |
| 3,539,034 | 11/1970 | Tafeen | 604/164 |
| 3,625,200 | 12/1971 | Muller | 128/772 |
| 3,661,148 | 5/1972 | Kolin | 128/774 X |
| 3,757,768 | 9/1973 | Kline | 128/DIG. 9 |
| 3,867,945 | 2/1975 | Long | 604/170 |
| 3,938,504 | 2/1976 | Dickinson et al. | 128/778 |
| 3,973,556 | 8/1976 | Fleischhacker et al. | 128/772 |
| 4,033,331 | 7/1977 | Gus et al. | 128/DIG. 9 |
| 4,299,226 | 11/1981 | Banka | 128/325 |

OTHER PUBLICATIONS

Kolin et al, IEEE Trans. on Bio-Med. Eng., vol. BME-18, No. 2, Mar. 1971, pp. 110-114.

Primary Examiner—Kyle L. Howell
Assistant Examiner—J. C. Hanley
Attorney, Agent, or Firm—Limbach, Limbach & Sutton

[57] ABSTRACT

A calibrator oval for the internal gauging of the lumen of a stenotic segment of artery is provided with an elongated carrier having a controllable variable flexibility.

2 Claims, 6 Drawing Figures

FLEXIBLE CALIBRATOR

This application is a continuation of application Ser. No. 114,979, filed Jan. 24, 1980.

BACKGROUND OF THE INVENTION

This invention relates to a flexible calibrator which is used to measure the diameter of the lumen in a stenotic segment of blood vessel when the vessel proximal to the stenosis is highly tortuous. At its distal end the calibrator is provided with a bulb-shaped or oval member which is used as a gauge member to determine the lumen size of the vessel.

The prior art known to me consists of the presently used calibrator instruments. They are provided with lumen-sizing ovals but are rigidly constructed. Their rigidity prevents them from being advanced through sharply winding segments of a vessel in order to reach and measure the desired area of stenosis.

SUMMARY OF THE INVENTION

A principal object of the invention is to provide a calibrator with a flexible shaft which enables the calibrator oval to be advanced through tortuous segments of a vessel in order to reach a given area of stenosis.

A further object of the invention is to provide a calibrator having an elongated carrier having variable stiffness and flexibility characteristics.

These objects are attained by providing the carrier with a flexible sheath member and a stiffener core member, the latter being withdrawable during use of the instrument so that an unstiffened, flexible portion of the sheath member may be passed through sharply winding segments of the vessel.

DESCRIPTION OF THE INVENTION

Figure 1:
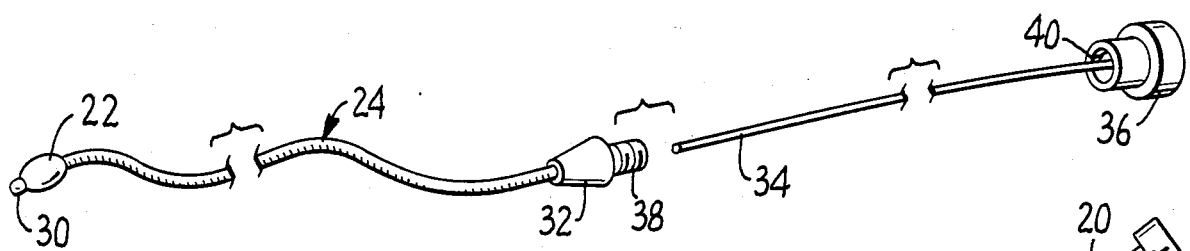
FIG. 1 is a view in perspective of the flexible calibrator of the invention.

A vessel 10 is provided with a proximal incision 12, an intermediate tortuous segment 14, and a distal stenotic segment 16 having a lumen 18 which is to be sized by use of the calibrator.

The calibrator comprises a handle 20, a calibrator oval 22 and a shaft or carrier 24 interconnecting the handle and oval. The shaft comprises a flexible sheath 26 formed of wound wire 28. The ends of the coiled wire 28 are suitable attached, as by soldering and cementing, to a rounded tip member 30 and to handle member 32. The carrier 24 further comprises a relatively stiff but flexible wire stiffener 34 for the flexible sheath 26. The stiffener wire is attached to handle member 36. Handle member 32 and 36 are adapted to be connected together as by threads 38 and 40. When the handle members 32 and 36 are connected together the distal end of wire 34 fits within socket 42 of tip member 30. The oval member 22 is formed of a soft, pliable material such as silicone.

Figure 2:
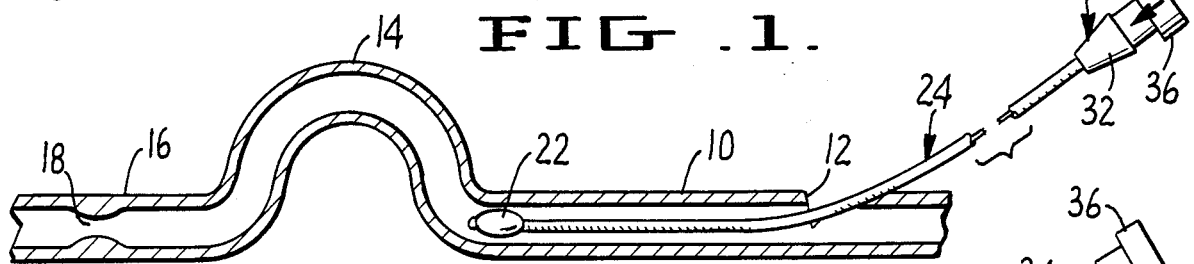
FIG. 2 shows the calibrator initially positioned for passage through a tortuous segment to a stenotic segment of a vessel.
Figure 3:
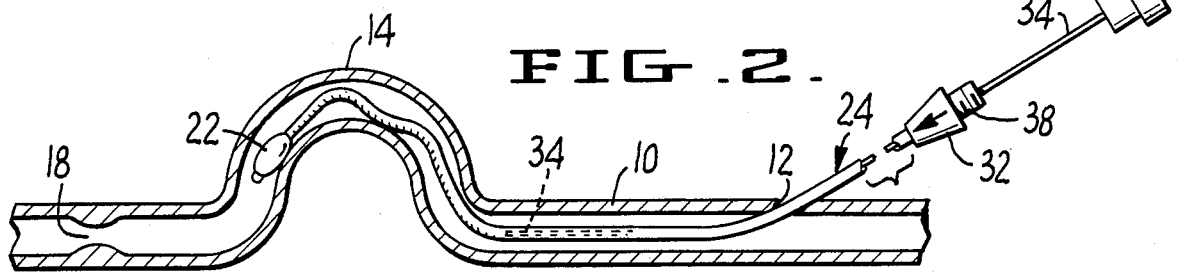
FIG. 3 is a similar view showing the instrument traversing the tortuous segment of the vessel.
Figure 4:
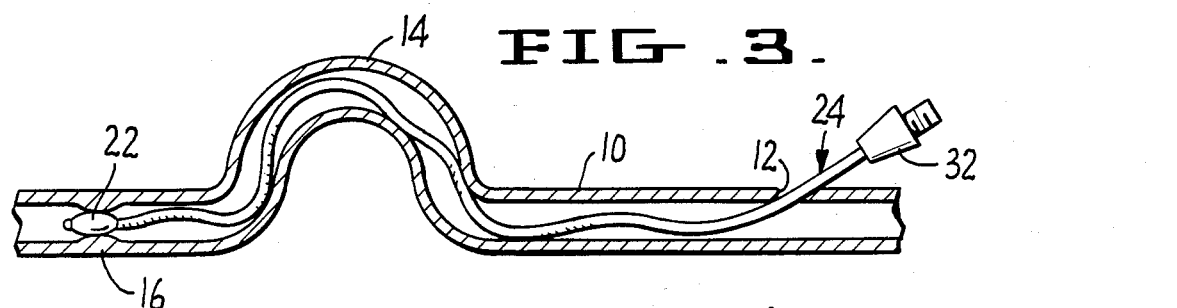
FIG. 4 is a similar view showing the calibrator oval of the instrument in sizing disposition to the stenotic segment of the vessel.

The manner of use of the calibrator is shown in FIGS. 2-4. In FIG. 2, the instrument has been introduced into the vessel 10 through the incision 12 and moved along the vessel to a point adjacent the tortuous segment 14. The wire 34 occupies the full length of the shaft or carrier 24. The stiffness of the shaft 24 is such that further movement of the instrument is resisted by the proximal end of the tortuous segment 14. The operator therefore backs the handle member 36 off of handle member 32 to withdraw enough of the length of the wire stiffener 34 from the flexible sheath 26 to enable the distal, unstiffened portion of sheath 26 to pass through the tortuous segment 14 as the instrument is fed along the vessel by movement of the handle member 32 toward incision 12. The oval 22 becomes finally positioned in the lumen 18 of stenotic segment 16. It typically requires the use of several such instruments, each with a calibration oval of a slightly different size, to correctly calibrate lumen 18.

The calibrator may be used with the wire stiffener 34 fully in place for the calibration of the lumen of a stenotic segment of a non-tortuous vessel. It may be used, as above described, when the vessel proximal to the stenosis is highly tortuous, sufficient length of the stiffener or stylet 34 being withdrawn from the shaft 24 in order to position the pliable calibrator oval 22 as shown in FIG. 4.

Figure 5:
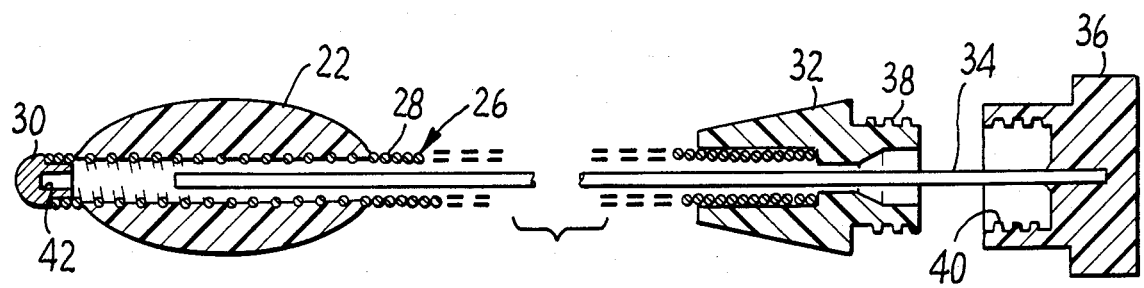
FIG. 5 is a view in elevation and in section of the preferred embodiment of the subject calibrator.

A preferred construction of the instrument is shown in FIG. 5. The turns of wire 28 are wound tightly upon each other throughout the length of sheat 26 except for that portion of the sheath which is contained within the oval 22. Here the turns of wire are spaced apart from each other such that the silicone material seeps into the lumen of the guide wire body during the molding process, thereby insuring that the oval 22 will not slip off of the guide wire during use of the calibrator.

Figure 6:
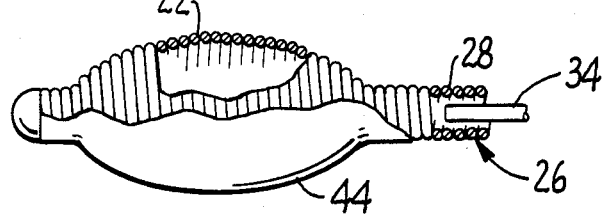
FIG. 6 is a broken-away view in elevation of a further embodiment of the subject calibrator.

A further embodiment of the instrument is shown in FIG. 6. Here the core of the oval 22 is formed of tightly wound turns of larger diameter of wire 28. The wire core of oval 22 is then covered with a thin plastic or silicone skin 44. The corrugated surface of the wire core of the oval serves as a good anchor for the skin 44.

In each of the embodiments of FIGS. 5-6, the oval has a pretermined generally constant diameter enabling it to serve as a guaging element, that is, as a lumen-sizing calibrator.

What is claimed is:

1. A device for measuring the degree of stenosis of arterial vessels comprising a flexible tubular shaft having a continuous generally imperforate side wall, a rounded tip member attached to said shaft as the distal end thereof, said tip member having an axial socket at its proximal end, an enlarged annular bulbous element forming part of said shaft and disposed adjacent said tip member, said element having a predetermined maximum diameter whereby said element serves as a lumen-sizing calibrator for an arterial vessel, a flexible stiffener member adapted to extend generally along the axis of said shaft for the full length thereof, said shaft and stiffener member having adjacently disposed complemental, interfittable and separable, handle portions at their proximal ends, said stiffener member having a distal end portion which interfits with the socket of said tip member when said handle portions are interfitted with each other, said stiffener member distal end portion and said socket being separated from each other when said handle portions are separated from each other.

2. The device of claim 1, said device being manipulatively threadable through arterial vessels by conjoint movement of said handle portions and by movement of one of said handle portions relative to the other of said handle portions.

* * * * *